Figure 1:
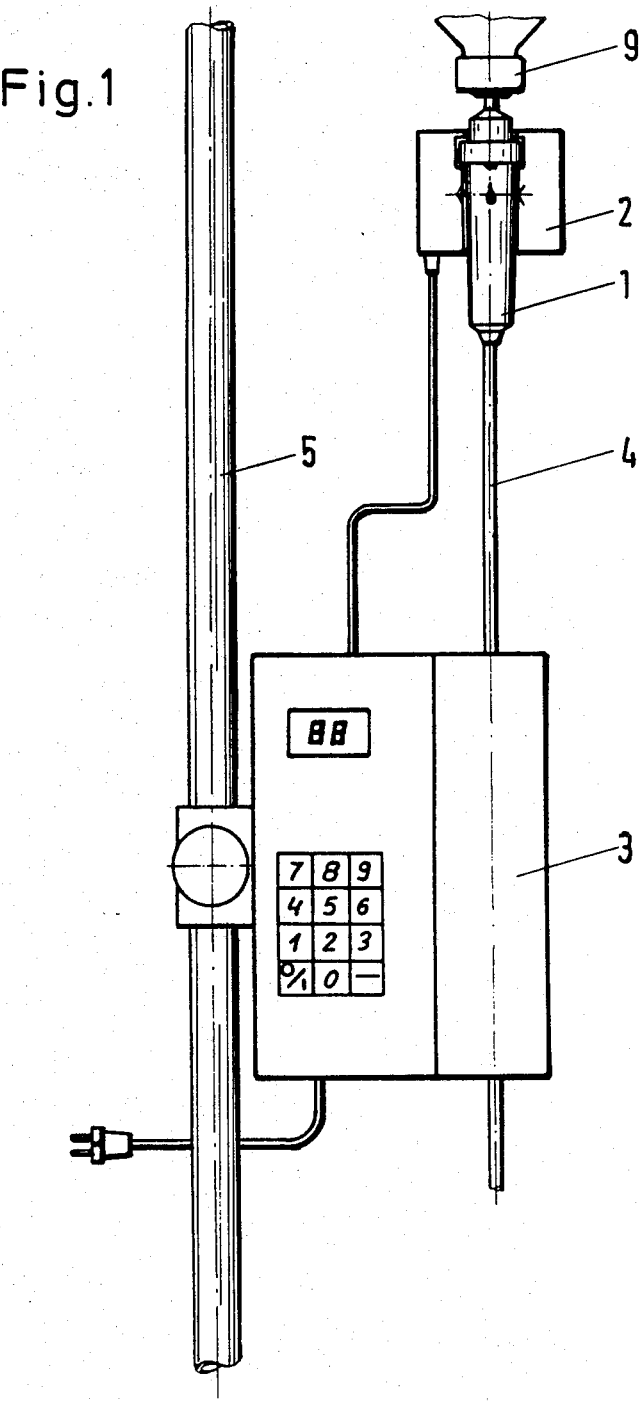

United States Patent [19]

Veracchi

[11] Patent Number: 4,652,262
[45] Date of Patent: Mar. 24, 1987

[54] GRAVITY INFUSION REGULATING APPARATUS

[75] Inventor: F. Baldo Veracchi, Hamburg, Fed. Rep. of Germany

[73] Assignee: Critikon GmbH, Norderstedt, Fed. Rep. of Germany

[21] Appl. No.: 698,329

[22] Filed: Feb. 5, 1985

[30] Foreign Application Priority Data

Feb. 7, 1984 [DE] Fed. Rep. of Germany ....... 3404144

[51] Int. Cl.$^4$ .............................................. A61M 5/00
[52] U.S. Cl. ........................... 604/250; 128/DIG. 13; 604/253
[58] Field of Search ............... 604/407, 250, 253, 256; 128/DIG. 12, DIG. 13

[56] References Cited

U.S. PATENT DOCUMENTS

| 4,137,940 | 2/1979 | Faisandier | 604/253 |
| 4,493,710 | 1/1985 | King et al. | 604/253 |
| 4,496,351 | 1/1985 | Hillel et al. | 604/250 |
| 4,551,134 | 11/1985 | Slavik et al. | 128/DIG. 13 |

Primary Examiner—Stephen C. Pellegrino
Attorney, Agent, or Firm—Erwin S. Teltscher; Peter R. Ruzek

[57] ABSTRACT

For use independent of a stand, a monolithic, miniaturized gravity infusion regulating apparatus comprises a single casing (6) housing the photoelectric drop detector (7), the electronics with controls (8) and the regulating mechanism and which can be fitted to the drop chamber (1) of an infusion instrument (FIG. 2).

4 Claims, 6 Drawing Figures

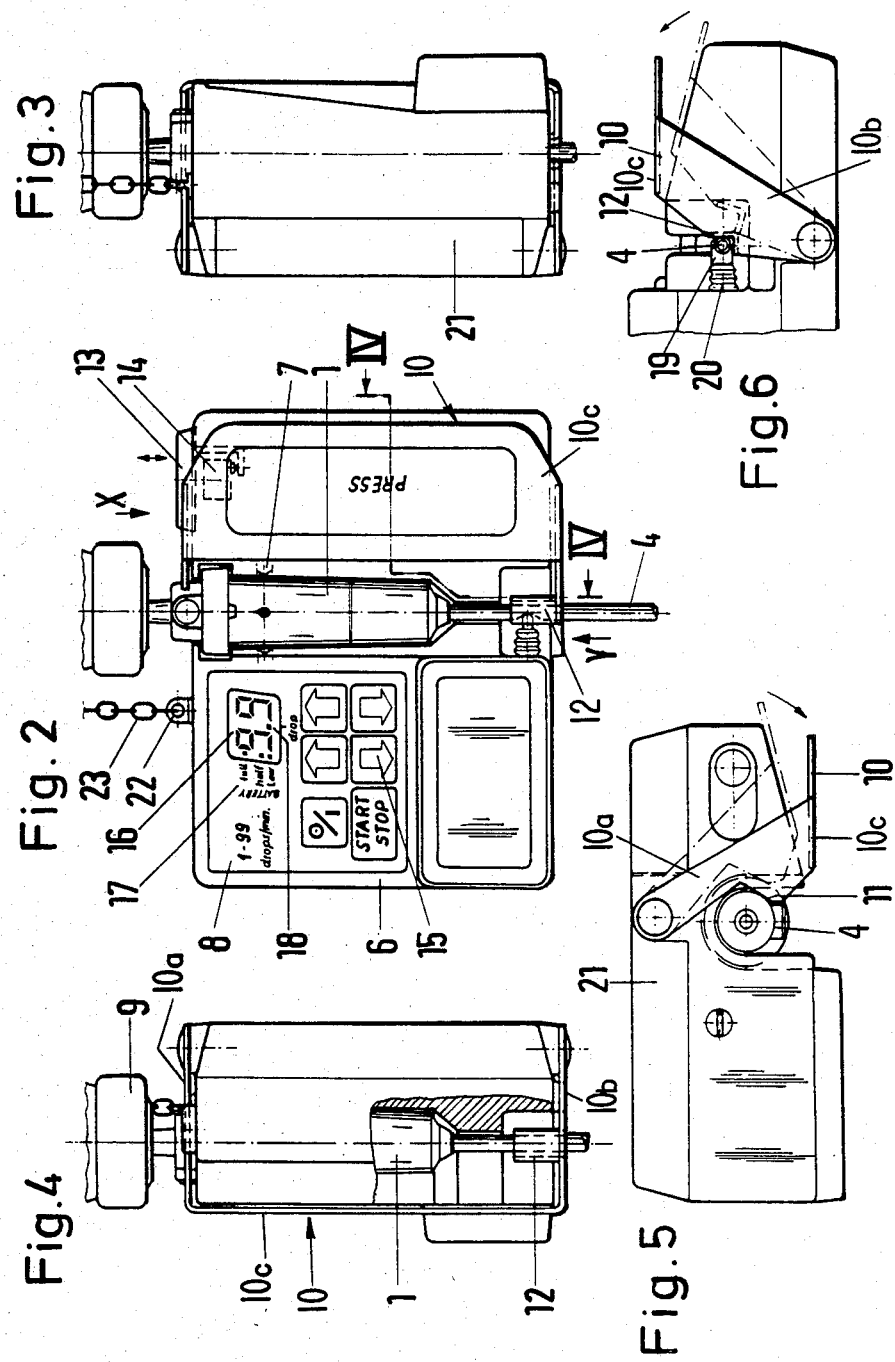

GRAVITY INFUSION REGULATING APPARATUS

The invention relates to a gravity infusion regulating apparatus.

Very varied constructions of gravity infusion regulating apparatuses are already in use, because they are less expensive than infusion pumps and lead to fewer risks for patients of the e.g. air embolism and extensive extravasal infiltration types. It is generally considered that more than 95% of all infusions can be carried out with a gravity infusion regulating apparatus and it would be highly desirable if virtually any infusion stand could be equipped with such an apparatus, because even 5% glucose infusion solution can be prejudicial to the patient if administered in an uncontrolled manner. The first obstacle to the hoped for wider use thereof is the relatively high price, which limits the use of this apparatus to intensive care wards or highly active solutions. The conventional roller clip, which is normally used for setting the drop rate, can only be looked upon as an aid because, quasi per axiom it is not very reliable and requires frequent monitoring and adjustment on the part of the overburdened, expensive nursing staff. The high price of conventional infusion regulating means is mainly due to the construction, which is fundamentally derived from that of an infusion pump and is diagrammatically shown in FIG. 1. A photoelectric drop sensor 2 is attached to the drop chamber 1 of an infusion instrument and determines the actual drop rate. This drop sensor is connected by a cable to the actual regulating device 3, so that the control electronics of the device by means of an electromechanical means influences the degree of occlusion of the infusion tube 4 and coincidence can be brought about between the actual drop rate and the set desired drop rate.

The hitherto known gravity infusion regulating apparatuses, which function with commercial infusion instruments are mains operated, frequently provided with a fixed rechargeable set of batteries which can only take over the emergency power supply for 3 to 4 hours and which requires 8 to 14 hours mains operation for recharging purposes. Such apparatuses are so large and so heavy, that they must be fixed to an infusion stand tube. There are also apparatuses which can be operated with a dry battery, so that the burdensome mains supply becomes superfluous. However, even these apparatuses, due to the dimensions and weight of the power supply must be attached to stands and suffer from the disadvantage that they require specially designed, expensive, cassette-like infusion instruments to enable them to make do with a low power consumption and consequently reduce the number of battery set replacement operations. Expensive battery operation also suffers from the disadvantage that the batteries have a limited storage life and it is consequently necessary to keep them continuously in stock.

The invention solves the problem of providing a lightweight, small and inexpensive, monolithic, miniaturized gravity infusion regulating apparatus, which is not standbound, is easy to operate and whose use can be extended down to peripheral wards.

For solving this problem, a gravity infusion regulating apparatus is proposed, which can be entirely fitted to the drop chamber of an infusion instrument and is constructed as a monolithic, miniaturized apparatus.

As a result of a gravity infusion regulating apparatus constructed in this way, the disadvantages of the known apparatuses are avoided.

Further advantageous developments of the invention can be gathered from the dependent claims.

The invention is described in greater detail hereinafter relative to the drawings, wherein show:

FIG. 1 in a diagrammatic view a stand-bound infusion regulating apparatus fixed to a known drop chamber of an infusion instrument.

FIG. 2 a front view of the infusion regulating apparatus according to the invention.

FIG. 3 a side view of the infusion regulating apparatus.

FIG. 4 a section along line IV—IV of FIG. 2.

FIG. 5 a view of the infusion regulating apparatus in the direction of arrow X in FIG. 2.

FIG. 6 a view of the infusion regulating apparatus in the direction of arrow Y in FIG. 2.

The infusion regulating apparatus shown in FIGS. 2 to 6 is constructed as follows. The two-part construction (drop sensor, regulating apparatus) is replaced by a monolithic construction and the photoelectric drop detector 7, the electronics with controls 8 and the regulating mechanism are enclosed in a single casing 6. As a result of appropriate constructional measures, the weight is limited to approximately 300 g, so that it can be directly attached to the drop chamber 1, whose puncture needle is secured so firmly in the rubber stopper of the infusion solution container 9, which is held in a holder 2 that it is able to withstand without difficulty tensile stresses of 500 to 600 g.

The front part of casing 6 is constructed in such a way that it can receive the contours of a drop chamber 1 in a positively engaging manner, the drop chamber 1 being inserted frontally. A fork-like lever 10, having an upper portion 10a and a lower portion 10b connected to one another by a handle 10c, is pivotably mounted on casing 6 so as to be juxtaposed with respective upper and lower parts of the casing 6, as can be seen from FIGS. 2 and 4 of the drawing; and is held by spring tension in the direction of fall, is on the one hand responsible for the securing of drop chamber 1 by being formed on its upper portion 10a with a suitable suitable contours, such as a notch 11 and on the other hand acts with its lower portion 10b as pivotable abutment 12 for squeezing the infusion tube 4 inserted into the casing 6. As can be seen from FIG. 2, the handle 10c is located at the front of the casing 6. To ensure that lever 10 is not operated unintentionally, probably leading to run-away, a knob-like closure 13 is provided, which must be pressed down before lever 10 with its abutment 12 can be pivoted from a rest position to an actuated position. It will be seen from FIG. 5 of the drawing, that the lever 10 must be in the actuated position—shown in dash-dot-dash lines—for the infusion tube to be inserted unhindered into the casing 6, as shown in the drawing, and that, as seen in FIG. 1 of the drawing, the infusion tube 4 is connected to the drop chamber 1.

Through the operation of a microswitch 14, a knob-like closure 13 also acts as an indicator for the correct position of lever 10 and logically also for the correct fitting of drop chamber 1 and infusion tube 4 enabling the electronics to give an alarm signal in the case of operating errors.

For space-saving reasons, keyboard 15 is in simplified form and it functions in the same way as a decoding switch operated by push buttons. A LED display of the drop rate 16, which lights up continuously or with different frequencies, also contains the battery charging state display 17 and indicates that a drop has fallen by decimal point 18 flashing.

The photoelectric drop detector 7, comprising a LED and a phototransistor, is integrated into casing 6, whilst the gear driven by a ministepping motor is designed in such a way that the in each case necessary safety requirements are fulfilled, a cam operating the regulating tongue 19 in order to permit variations to the degree of occlusion of the infusion tube 4, as can be seen from FIG. 2 of the drawing. As can be seen from FIG. 6, the lower portion 10b of the lever 10 acts as an abutment, when the cam operating the tongue 19 squeezes the infusion tube 4 thereagainst. The apparatus is appropriately protected by means, such as a bellows 20 and other suitable sealing elements against backwater surges and can consequently be easily cleaned, whilst it is also protected against any outflow of the infusion solution.

The battery box 21 containing the NiCd elements and which, for purposes of easier interchangeability, is held by means of permanent magnets with relative opposite poles provided in the casing recesses and battery box, respectively. The battery box is dimensioned in such a way that at least 24 hours battery operation is guaranteed. During this time, a second battery box is fully charged in a separate charger in approximately 14 hours, so that uninterrupted operation with an adequate safety margin is ensured. Through the suitable choice of the electronic components and the display elements, the circuit is designed in such a way that power consumption is minimized. A chain 23 is fitted to a ring 22 and can be fixed to the bottle holder, in order to prevent any accidental dropping of the apparatus.

I claim:

1. Gravity infusion regulating apparatus, comprising in combination,
   a casing having a front part thereof formed with a notch corresponding to a contour of a drop chamber for frontal insertion of the drop chamber into said casing,
   a photoelectric sensor being received in a seat of said casing, said casing also enclosing electronics with controls and a regulating mechanism,
   a fork-like lever being pivotably mounted on said casing and held thereto by spring tension, said lever having an upper portion and a lower portion connected by a handle to said upper portion, said handle being located in a front portion of said casing, said lever being movable between a rest position and an actuated position,
   said upper lever portion being formed with an indentation corresponding to said notch for receiving said drop chamber, said lower lever portion having an abutment, including a regulating tongue, for squeezing an infusion tube, said infusion tube being insertable free of any hindrance into said casing in the actuated position of said lever when said abutment is spaced from said infusion tube, while the abutment of said lever squeezes said infusion tube by means of said regulating tongue in the rest position of said lever, said lever being protected against any unintentional operation by a knob-like closure abutting said upper lever portion.

2. The gravity infusion regulating apparatus according to claim 1, wherein through operation of a microswitch, said closure also acts an an indicator for correct positioning of said lever, and for correct fitting of said drop chamber into said casing, enabling said electronics to give an alarm signal in the case of any operating errors, including incorrect positioning of said case and incorrect fitting of said drop chamber.

3. The gravity infusion regulating apparatus according to claim 2, wherein said casing is provided with a recess, and further comprising a battery box held in said recess by means of permanent magnets with relative opposite poles provided in the casing recess and battery, respectively.

4. The gravity infusion regulating apparatus according to claim 1 further comprising a chain secured to said casing and adapted to be fixed to a holder for a container of infusion solution, said container being located above said casing.

* * * * *